United States Patent
Sakai et al.

(10) Patent No.: US 10,088,669 B2
(45) Date of Patent: Oct. 2, 2018

(54) ENDOSCOPE

(71) Applicant: OLYMPUS CORPORATION, Tokyo (JP)

(72) Inventors: Youhei Sakai, Ina (JP); Hideharu Miyahara, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 149 days.

(21) Appl. No.: 15/148,203

(22) Filed: May 6, 2016

(65) Prior Publication Data
US 2016/0246049 A1 Aug. 25, 2016

Related U.S. Application Data

(63) Continuation of application No. PCT/JP2014/074545, filed on Sep. 17, 2014.

(30) Foreign Application Priority Data

Nov. 18, 2013 (JP) .................... 2013-238241

(51) Int. Cl.
| | |
|---|---|
| *H04N 7/18* | (2006.01) |
| *G02B 23/24* | (2006.01) |
| *G02B 23/26* | (2006.01) |
| *A61B 1/00* | (2006.01) |
| *A61B 1/05* | (2006.01) |

(Continued)

(52) U.S. Cl.
CPC .......... *G02B 23/2484* (2013.01); *A61B 1/005* (2013.01); *A61B 1/00013* (2013.01);
(Continued)

(58) Field of Classification Search
CPC ............ G02B 23/2484; G02B 23/2423; G02B 23/26; G02B 23/2476; G02B 6/4243;
(Continued)

(56) References Cited

U.S. PATENT DOCUMENTS

2004/0158159 A1* 8/2004 Seto ...................... A61B 1/0051
600/476
2007/0260113 A1* 11/2007 Otawara ............ A61B 1/00091
600/104

(Continued)

FOREIGN PATENT DOCUMENTS

| JP | 63-115532 A | 5/1988 |
|---|---|---|
| JP | H02-135313 A | 5/1990 |

(Continued)

OTHER PUBLICATIONS

International Search Report dated Oct. 28, 2014 issued in PCT/JP20141074545.

(Continued)

*Primary Examiner* — Allen C Wong
(74) *Attorney, Agent, or Firm* — Scully, Scott, Murphy & Presser, P.C.

(57) ABSTRACT

An endoscope includes an insertion section in which a rigid distal end portion, a bending section for changing a direction of the rigid distal end portion, and a flexible portion are concatenated and an optical fiber that transmits an optical signal, the optical fiber being inserted through an inside of the insertion section. The rigid distal end portion is provided with an image pickup device, an optical element that converts an electric signal outputted by the image pickup device into the optical signal, a holding member including a through-hole, into which a distal end portion of the optical fiber is inserted, and a wiring board on which the optical element is mounted and to which the holding member is joined. The optical fiber is inserted through a center of the bending section.

5 Claims, 9 Drawing Sheets

(51) Int. Cl.
  *G02B 6/42* (2006.01)
  *A61B 1/005* (2006.01)
(52) U.S. Cl.
  CPC ............... *A61B 1/05* (2013.01); *A61B 1/051* (2013.01); *G02B 6/4243* (2013.01); *G02B 23/2423* (2013.01); *G02B 23/2476* (2013.01); *G02B 23/26* (2013.01)
(58) Field of Classification Search
  CPC ........... A61B 1/005; A61B 1/051; A61B 1/05; A61B 1/00013
  USPC ........................................................ 348/68
  See application file for complete search history.

(56) References Cited

U.S. PATENT DOCUMENTS

| | | | |
|---|---|---|---|
| 2009/0203966 A1* | 8/2009 | Mizuyoshi | A61B 1/00096 600/182 |
| 2011/0230716 A1* | 9/2011 | Fujimoto | A61B 1/00135 600/121 |
| 2013/0182099 A1 | 7/2013 | Nakamura | |
| 2014/0097459 A1 | 4/2014 | Motohara | |

FOREIGN PATENT DOCUMENTS

| | | |
|---|---|---|
| JP | 6-133921 A | 5/1994 |
| JP | 8-160315 A | 6/1996 |
| JP | 2010-000186 A | 1/2010 |
| JP | 2010-194037 A | 9/2010 |
| JP | 2013-25092 | 2/2013 |
| WO | WO 2013/011983 A1 | 1/2013 |

OTHER PUBLICATIONS

Extended Supplementary European Search Report dated Jun. 21, 2017 in European Patent Application No. 14 86 2426.5.

* cited by examiner

10,088,669 B2

ENDOSCOPE

CROSS REFERENCE TO RELATED APPLICATION

This application is a continuation application of PCT/JP2014/074545 filed on Sep. 17, 2014 and claims benefit of Japanese Application No. 2013-238241 filed in Japan on Nov. 18, 2013, the entire contents of which are incorporated herein by this reference.

BACKGROUND OF INVENTION

1. Field of the Invention

The present invention relates to a flexible endoscope in which an optical fiber of a light transmission module provided at a rigid distal end portion is inserted through an insertion section.

2. Description of the Related Art

An endoscope includes an image pickup device such as a CCD at a rigid distal end portion of an elongated flexible insertion section. In recent years, use of an image pickup device having a large number of pixels in an endoscope has been examined. When the image pickup device having the large number of pixels is used, a signal amount transmitted from the image pickup device to a signal processing apparatus (a processor) increases. Therefore, optical signal transmission via a thin optical fiber by an optical signal is desirably performed instead of electric signal transmission via a metal wire by an electric signal. For the optical signal transmission, an E/O module (an electro-optical converter) that converts an electric signal into an optical signal and an O/E module (a photoelectric converter) that converts the optical signal into an electric signal are used.

For example, Japanese Patent Application Laid-Open Publication No. 2013-025092 discloses a light transmission module including an optical element that performs input or output of an optical signal, a substrate mounted with the optical element, a holding section including a through-hole for optical fiber insertion for transmitting the optical signal inputted to and outputted from the optical element and disposed along a thickness direction of the optical element.

SUMMARY OF THE INVENTION

An endoscope according to an embodiment of the present invention includes: an insertion section in which a rigid distal end portion, a bending section for changing a direction of the rigid distal end portion, and a flexible portion are concatenated; and an optical fiber that transmits an optical signal, the optical fiber being inserted through an inside of the insertion section. The rigid distal end portion is provided with an image pickup device, an optical element including a light emitting section that converts an electric signal outputted by the image pickup device into the optical signal, a holding member including a through-hole, into which a distal end portion of the optical fiber is inserted, and disposed to locate the through-hole on the light emitting section, and a wiring board on which the optical element is mounted and to which the holding member is joined. The optical fiber is inserted through a center of the bending section.

DETAILED DESCRIPTION OF THE PREFERRED EMBODIMENT(S)

First Embodiment

Figure 1:
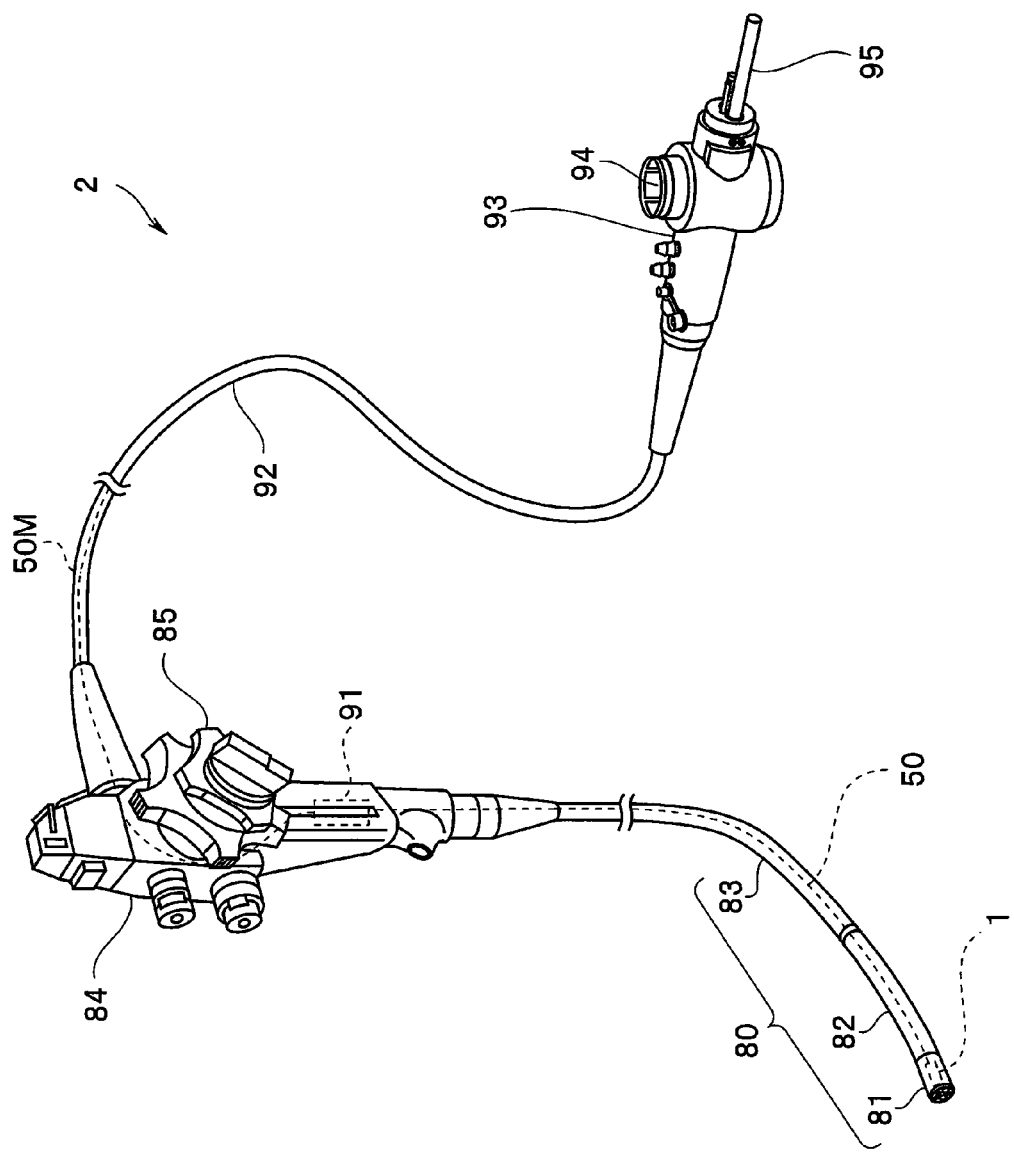
FIG. 1 is a perspective view of an endoscope in a first embodiment.

As shown in FIG. 1, an endoscope 2 in the present embodiment is a flexible electronic endoscope including an insertion section 80, an operation section 84 provided on a proximal end side of the insertion section 80, a universal cord 92 extended from the operation section 84, and a connector 93 provided on a proximal end side of the universal cord 92.

In the insertion section 80, a rigid distal end portion 81, a bending section 82 for changing a direction of the rigid distal end portion 81, and an elongated flexible portion 83 having flexibility are concatenated in order.

In the rigid distal end portion 81, a not-shown image pickup optical unit, an image pickup device 90 (FIG. 3), and a light transmission module 1, which is an E/O module that converts an image pickup signal (an electric signal) from the image pickup device 90 (FIG. 3) into an optical signal, are provided. The image pickup device 90 is a CMOS (complementary metal oxide semiconductor) image sensor, a CCD (charge coupled device), or the like.

Figure 2:
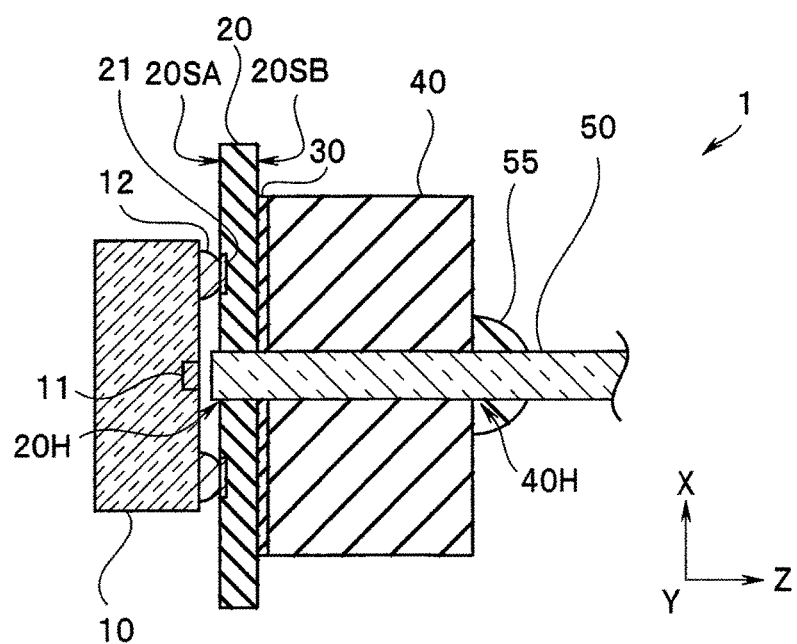
FIG. 2 is a sectional view of a light transmission module of the endoscope in the first embodiment.

As shown in FIG. 2, the light transmission module 1 includes an optical element 10, a wiring board 20, a holding member (also referred to as ferrule) 40, and an optical fiber 50. In the light transmission module 1, the optical element 10, the wiring board 20, and the holding member 40 are disposed side by side in a thickness direction of the optical element 10 (a Z direction). That is, the optical element 10 is mounted on and the holding member 40 is joined to the wiring board 20.

The optical element 10 is a surface emission laser chip including a light emitting section 11 that outputs light of an optical signal. For example, the very-small optical element 10 having a plan view dimension of 250 μm×300 μm includes, on a principal plane, the light emitting section 11 having a diameter of 20 μm and electrodes 12 that supply a driving signal to the light emitting section 11.

On the other hand, for example, the optical fiber 50 having a diameter of 125 μm includes a core having a diameter of 50 μm that transmits light and a clad that covers an outer circumference of the core.

A distal end portion of the optical fiber 50 is inserted into a through-hole 40H of the substantially rectangular parallelepiped holding member 40 bonded on the optical element 10 and is fixed by an adhesive 55. Positioning of the light emitting section 11 of the optical element 10 and the optical fiber 50 is performed by inserting the optical fiber 50 into the through-hole 40H.

A hole 20H functioning as an optical path is present in the flat wiring board 20 including a first principal plane 20SA and a second principal plane 20SB. The optical element 10 is flip-chip mounted on the first principal plane 20SA in a state in which the light emitting section 11 of the optical element 10 is disposed in a position opposed to the hole 20H of the wiring board 20. That is, the wiring board 20 includes electrode pads 21 respectively joined to a plurality of electrodes 12 of the optical element 10. As a base of the wiring board 20, an FPC substrate, a ceramic substrate, a glass epoxy substrate, a glass substrate, a silicon substrate, or the like is used.

For example, Au bumps, which are the electrodes 12 of the optical element 10, are joined to the electrode pads 21 of the wiring board 20 by ultrasound. Note that an adhesive such as an under-fill material or a side-fill material may be injected into joining sections.

After printing solder paste or the like and disposing the optical element 10 in a predetermined position, solder may be melted by a reflow or the like to mount the optical element 10 on the wiring board 20. Note that the wiring board 20 includes an electrode pad (not shown in the figure) connected to the image pickup device 90 (FIG. 3) by a metal wire 90M (FIG. 3) and a wire (not shown in the figure) that transmits an electric signal transmitted from the image pickup device 90 to the electrode pad 21. The wiring board 20 may include a processing circuit for converting the electric signal transmitted from the image pickup device 90 into a driving signal for the optical element 10.

As explained above, in the holding member 40, the columnar through-hole 40H having an inner diameter substantially the same as an outer diameter of the optical fiber 50 inserted into the through-hole 40H is formed. "Substantially the same" means that both the diameters are substantially the "same" size for setting an outer circumferential surface of the optical fiber 50 and a wall surface of the through-hole 40H to a contact state. For example, the inner diameter of the through-hole 40H is manufactured larger than the outer diameter of the optical fiber 50 by 1 μm to 5 μm.

The through-hole 40H may have a prism shape other than the columnar shape as long as the optical fiber 50 can be held by the wall surface of the through-hole 40H. A material of the holding member 40 is ceramic, Si, glass, a metal member such as SUS, or the like. Note that the holding member 40 may have a substantially columnar shape or a substantially conical shape.

The holding member 40 is joined to the second principal plane 20SB of the wiring board 20 via an adhesive layer 30 in a state in which the through-hole 40H is disposed in a position opposed to the hole 20H of the wiring board 20. Note that, for example, the adhesive layer 30 made of thermosetting resin is not provided in an opposed region of the through-hole 40H and the hole 20H.

An angle knob 85 for operating the bending section 82 is provided in the operation section 84. An O/E module 91, which is a light transmission module that converts an optical signal into an electric signal, is provided in the operation section 84. The connector 93 includes an electric connector section 94 connected to a processor (not shown in the figure) and a light-guide connecting section 95 connected to a light source. The light-guide connecting section 95 is connected to an optical fiber bundle that guides illumination light to the rigid distal end portion 81. Note that, in the connector 93, the electric connector section 94 and the light-guide connecting section 95 may be integrated.

In the endoscope 2, an image pickup signal is converted into an optical signal by the light transmission module 1 of the rigid distal end portion 81 and transmitted to the operation section 84 via the thin optical fiber 50 inserted through the insertion section 80. The optical signal is converted into an electric signal again by the O/E module 91 provided in the operation section 84 and is transmitted to the electric connector section 94 via a metal wire 50M inserted through the universal cord 92. That is, a signal is transmitted via the optical fiber 50 in the small-diameter insertion section 80. The signal is transmitted via the metal wire 50M thicker than the optical fiber 50 in the universal cord 92 that is less limited in an outer diameter without being inserted into a body.

Note that, when the O/E module 91 is disposed in the connector section 94, the optical fiber 50 may be inserted through the universal cord 92 to the electric connector section 94. When the O/E module 91 is provided in the processor, the optical fiber 50 may be inserted through to the connector 93.

It is likely that, when the insertion section 80 is deformed, stress is applied to the optical fiber 50 inserted through the insertion section 80 of the endoscope 2. The optical fiber does not have high strength in a longitudinal direction. Therefore, according to deformation of the flexible insertion section of the endoscope, when tensile stress/compression stress is repeatedly applied in the longitudinal direction of the optical fiber, it is likely that the optical fiber is damaged or broken. It is also likely that other members present in the insertion section and the optical fiber are entangled with each other and the optical fiber is damaged or receives torsional stress. When the optical fiber is, for example, damaged, it is difficult to transmit the optical signal.

The optical fiber 50 is likely to receive large stress, in particular, from deformation due to bending operation of the bending section 82.

Figure 3:
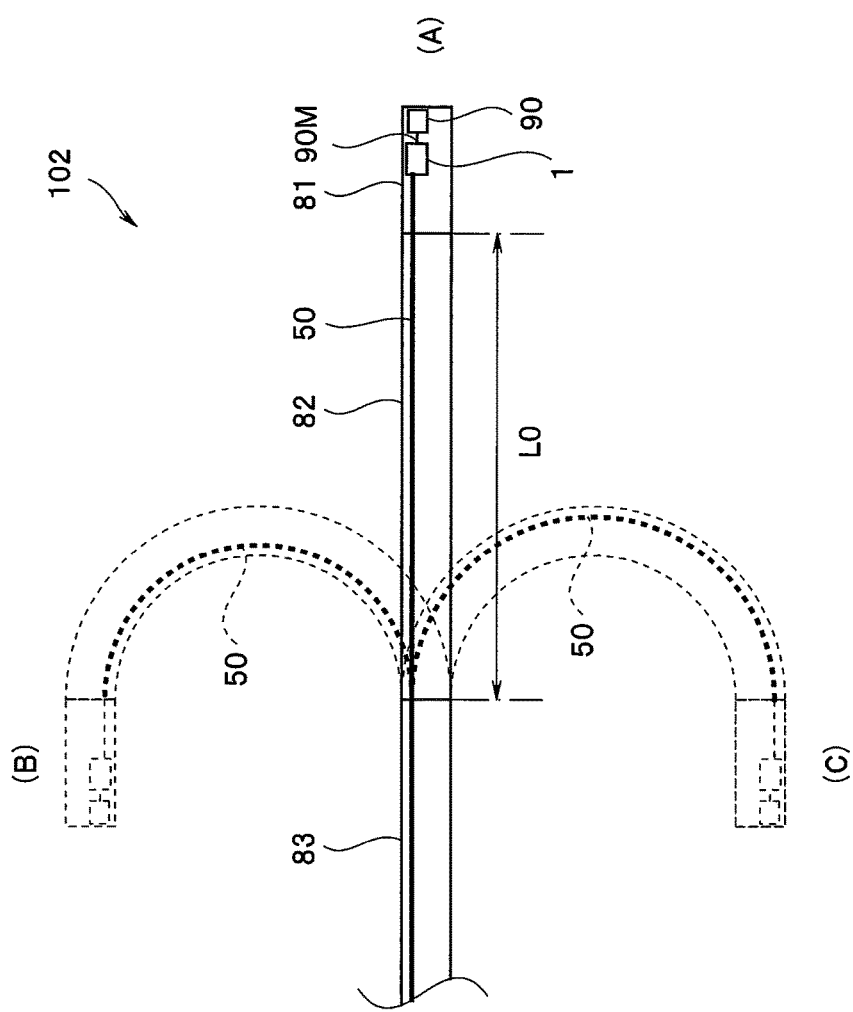
FIG. 3 is a sectional view showing a motion of a bending section of a conventional endoscope.

For example, as shown in FIG. 3, in a conventional endoscope 102, route length L in which the optical fiber 50 is inserted through when the bending section 82 is in a linear state (A) is represented as L0. On the other hand, when the bending section 82 bends in a (B) direction, since the route length L decreases, it is likely that compression stress is applied to the optical fiber 50. On the other hand, when the bending section 82 bends in a (C) direction, since the route length L increases, it is likely that tensile stress is applied to the optical fiber 50.

Figure 4:
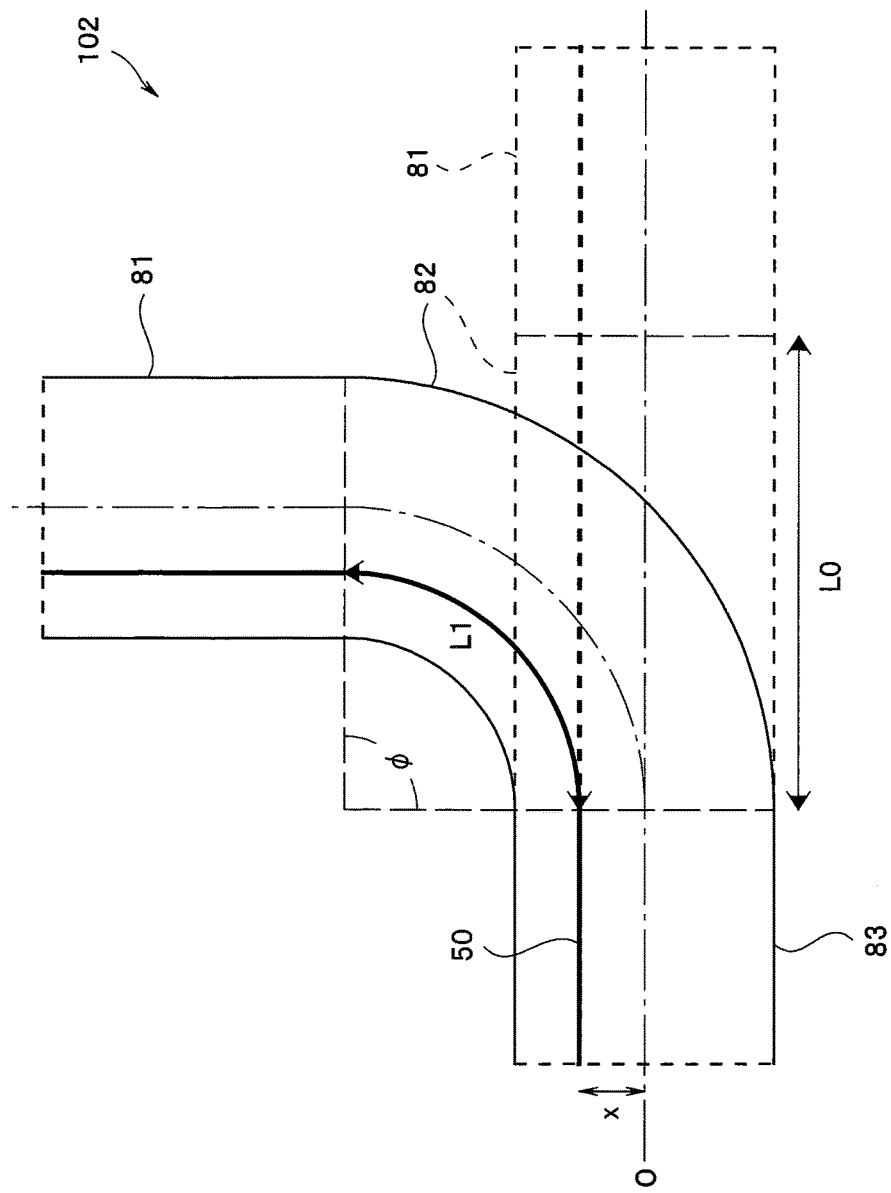
FIG. 4 is a sectional view showing a motion of the bending section of the conventional endoscope.

In the following explanation, as shown in FIG. 4, in the conventional endoscope 102, the bending section 82 bends in the (B) direction and a bending angle is an angle $\phi$. As a premise, it is assumed that, even if a scope bends, length of a scope center (x=0) does not change from L0. When an insert-through route of a center of the optical fiber 50 is apart from a center line (a center axis) O of the bending section 82 by a deviation amount x, the route length L decreases from L0 to L1.

$$L1 = L0 - \Delta L \tag{Equation 1}$$

where, $\Delta L = 2\pi x (\phi/360)$

That is, $\Delta L$ depends on the deviation amount x and the bending angle $\phi$. For example, $\Delta L = 15$ mm at the deviation amount x=5 mm and the bending angle φ=180 degrees. Note that a maximum bending angle φmax of the bending section 82 is different depending on specification and is sometimes 360 degrees or more.

Figure 5:
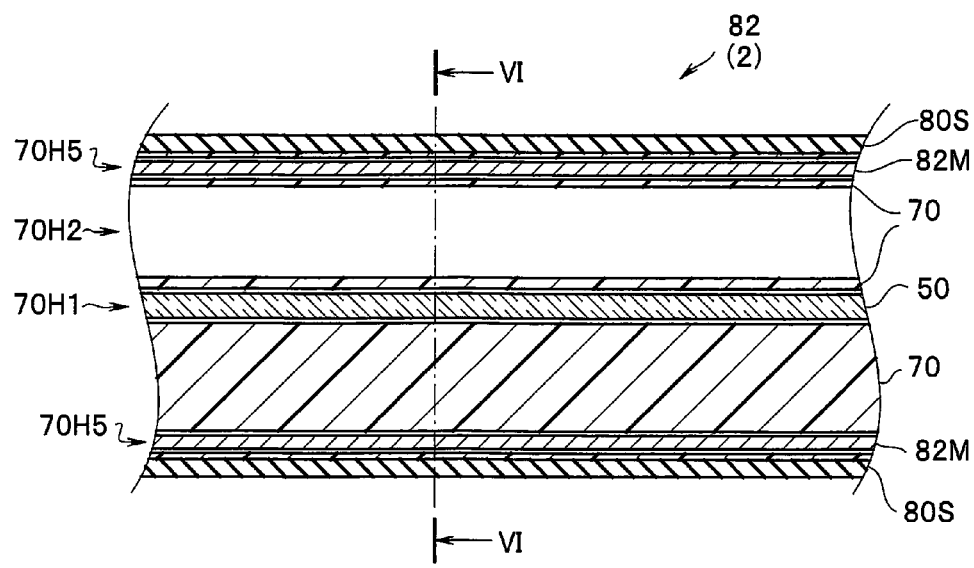
FIG. 5 is a sectional view in a longitudinal direction of a bending section of the endoscope in the first embodiment.
Figure 6:
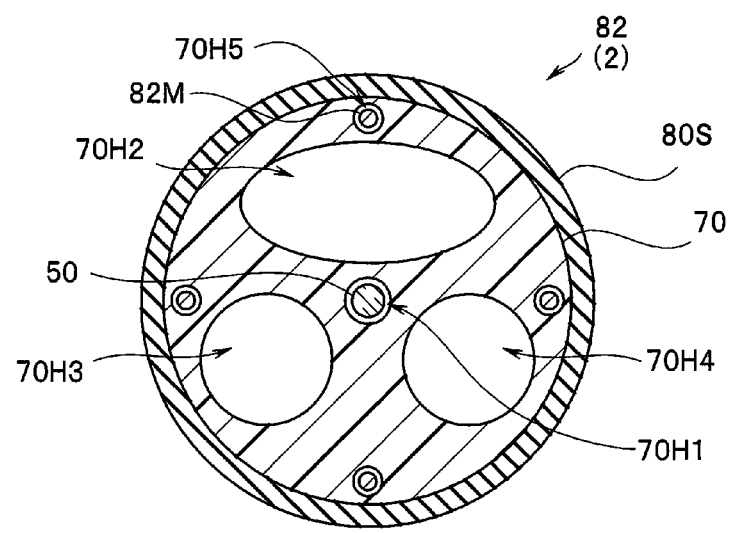
FIG. 6 is a sectional view taken along VI-VI line in FIG. 5 of the bending section of the endoscope in the first embodiment.

As shown in FIG. 5 and FIG. 6, in the endoscope 2 in the embodiment, a multi-lumen tube 70, in which a plurality of hole paths 70H1 to 70H5 are formed, is provided on an inside of an outer circumferential section 80S of the bending section 82. The optical fiber 50 is inserted through the hole path 70H1 inserted through a center of the bending section 82.

Note that, although not shown in the figure, electric wires, channels, and the like are inserted through the hole paths 70H2 to 70H4. Operation wires 82M for a bending operation of the bending section 82 are respectively inserted through the four hole paths 70H5.

The multi-lumen tube 70 is made of flexible resin such as polyamide, polyester, polyurethane, polystyrene, fluorine-based resin, silicone rubber, or latex rubber.

Figure 7:
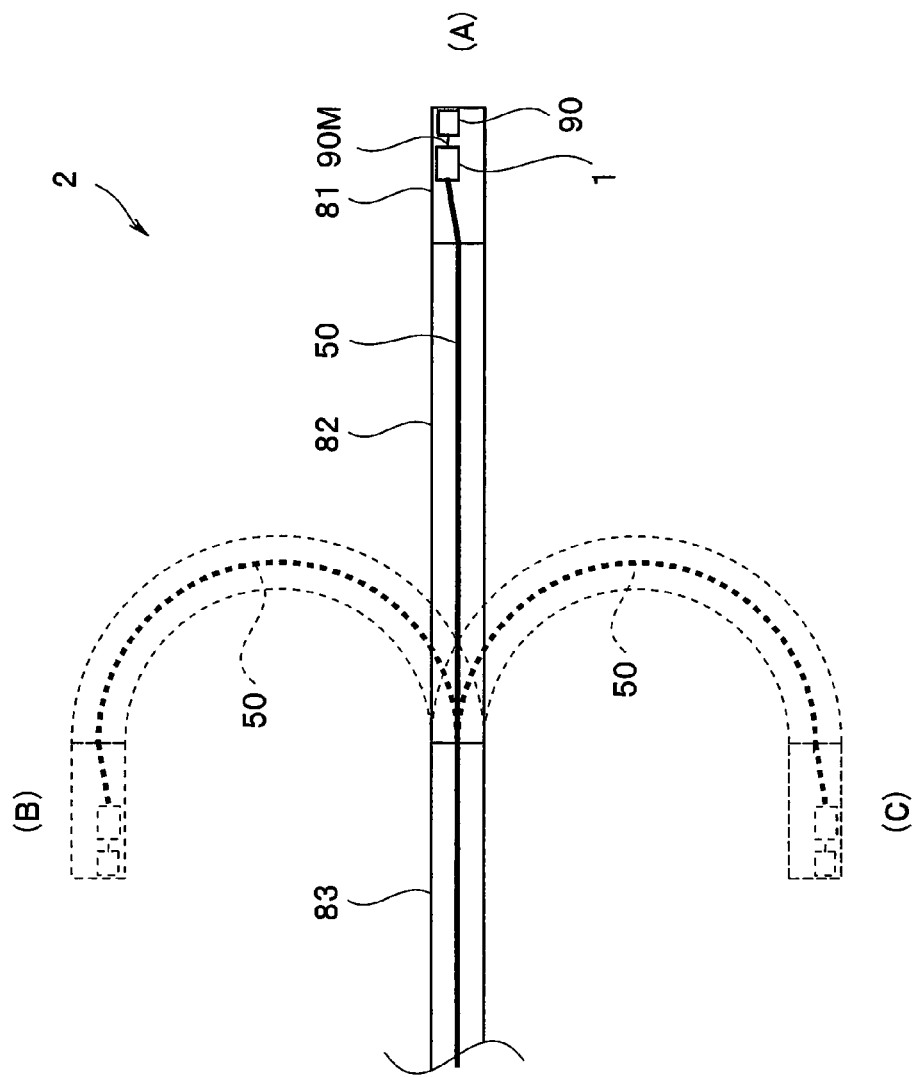
FIG. 7 is a sectional view showing a motion of the bending section of the endoscope in the first embodiment.

As shown in FIG. 7, in the endoscope 2 in the embodiment, the optical fiber 50 is inserted through the center of the bending section 82. The center means a center of a circle of a cross section orthogonal to a longitudinal direction of the bending section 82. That is, the optical fiber 50 is disposed to set the deviation amount x to nearly zero.

In the endoscope 2, in FIG. 5, irrespective of whether the bending section 82 bends in the (A) direction or bends in the (B) direction, ΔL=0. Stress is not applied to the optical fiber 50.

Note that, since stress applied to the optical fiber 50 is smaller as the deviation amount x is smaller, the deviation amount x is most desirably x=0 but does not have to be x=0. That is, the deviation amount x is selectable according to, for example, specifications of the endoscope. However, x only has to be 3 mm or less and is desirably 1 mm or less.

Since large stress is not applied to the optical fiber 50 even if the bending section 82 is deformed, the endoscope 2 can stably transmit an optical signal.

Note that the optical fiber 50 in a portion inserted through the flexible portion 83 is also desirably inserted through a center of the flexible portion 83. This is because stress is not applied to the optical fiber 50 by deformation of the flexible portion 83.

Modification of the First Embodiment

Figure 8:
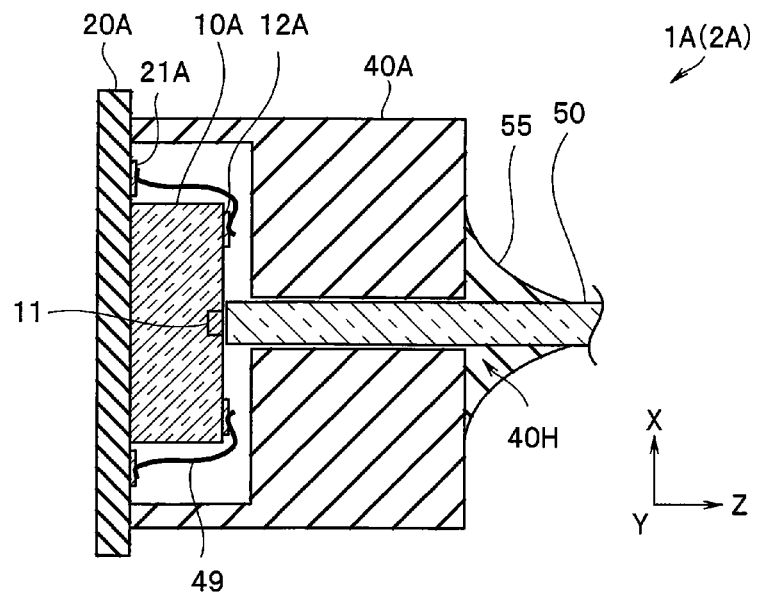
FIG. 8 is a sectional view of a light transmission module of an endoscope in a modification of the first embodiment.

An endoscope 2A in a modification includes a light transmission module 1A shown in FIG. 8.

In the light transmission module 1A, an optical element 10A and a holding member 40A are provided on one surface of a wiring board 20A. Electrodes 12A of the optical element 10A and electrode pads 21A of the wiring board 20A are connected by wire bonding wires 49.

The holding member 40A having a recess, in which the optical element 10A is housed, is joined to the wiring board 20A via a bonding layer (not shown in the figure) such that the through-hole 40E1 is opposed to the light emitting section 11 of the optical element 10A.

In the light transmission module 1A, it is unnecessary to provide a hole functioning as an optical path in the wiring board. Two components, that is, the optical element 10A and the holding member 40A only have to be aligned. Therefore, manufacturing is easy.

That is, the optical element 10A only has to be mounted on and the holding member 40A only has to be joined to the wiring board of the endoscope 2A.

Second Embodiment

An endoscope 2B in a second embodiment is similar to the embodiment 2 and the like. Therefore, components having the same functions are denoted by the same reference numerals and signs and explanation of the components is omitted.

Figure 9:
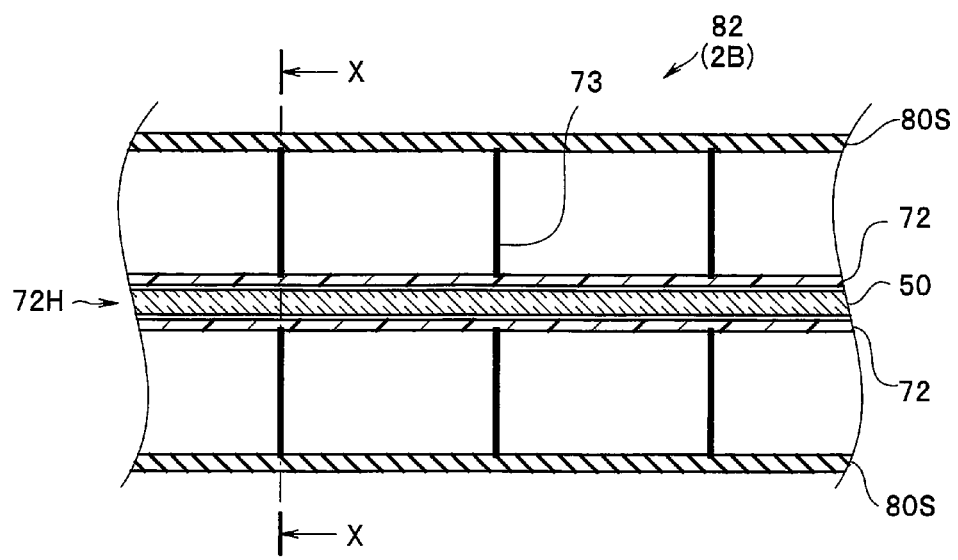
FIG. 9 is a sectional view in a longitudinal direction of a bending section of an endoscope in a second embodiment.
Figure 10:
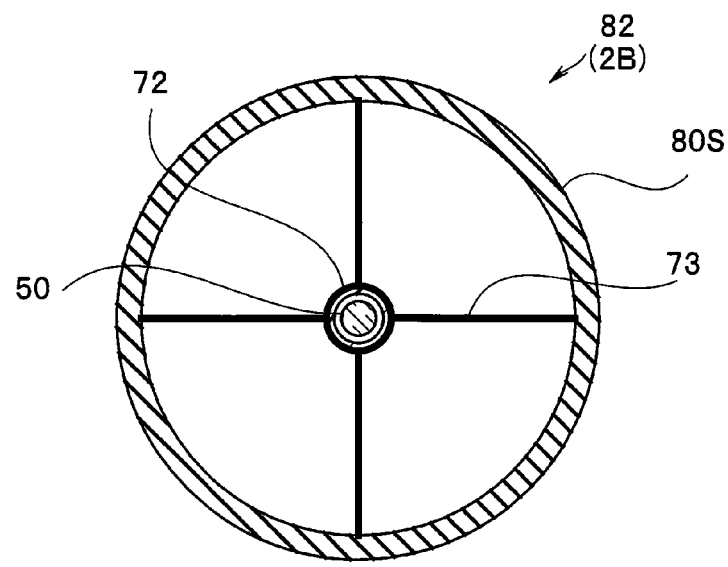
FIG. 10 is a sectional view taken along X-X line in FIG. 9 of the bending section of the endoscope in the second embodiment.

As shown in FIG. 9 and FIG. 10, in the bending section 82 of the endoscope 2B, a tube 72 including the hole path 72H is disposed in the center of the bending section 82 by a plurality of supporting members 73. The supporting members 73, four arms of which are fixed on an inner surface of the outer circumferential section 80S of the bending section 82, are disposed at a predetermined interval. A disposition interval of the supporting members 73 is, for example, ⅓ to 1/10 of length of the bending section 82.

The optical fiber 50 is inserted through the hole path 72H of the tube 72.

In the endoscope 2B, as in the endoscope 2, the optical fiber 50 is inserted through the center of the bending section 82. Therefore, since large stress is not applied to the optical fiber 50 even if the bending section 82 is deformed, the endoscope 2B can stably transmit an optical signal.

The bending section 82 of the endoscope 2B is not a lumen tube. Therefore, since a degree of freedom of disposition of other members on an inside of the bending section 82 is higher than the degree of freedom in the endoscope 2, design is easy.

Note that the tube 72 held by the supporting members 73 may be provided in the flexible portion 83 as well. A disposition interval of the supporting members 73 in the flexible portion 83 may be longer than the disposition interval in the bending section 82.

Third Embodiment

An endoscope 2C in a third embodiment is similar to the endoscope 2 and the like. Therefore, components having the same functions are denoted by the same reference numerals and signs and explanation of the components is omitted.

Figure 11:
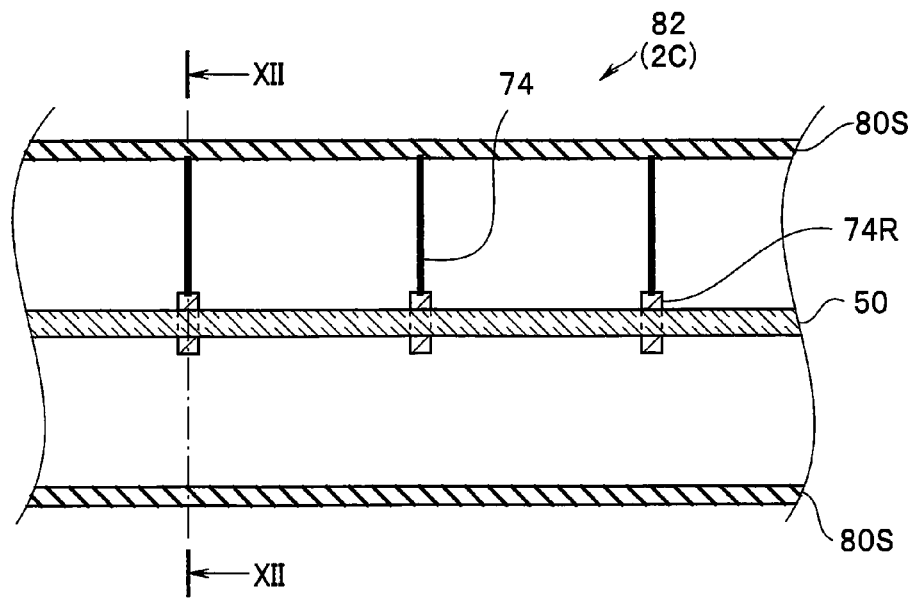
FIG. 11 is a sectional view in a longitudinal direction of a bending section of an endoscope in a third embodiment.
Figure 12:
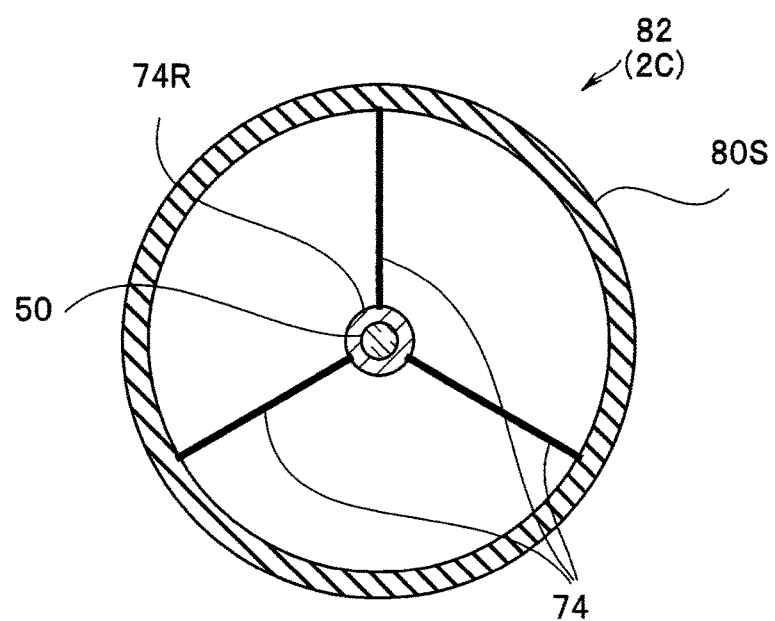
FIG. 12 is a sectional view taken along XII-XII line in FIG. 9 of the bending section of the endoscope in the third embodiment.

As shown in FIG. 11 and FIG. 12, in the bending section 82 of the endoscope 2C, a plurality of supporting members 74 including rings 74R are fixed to the outer circumferential section 80S such that the rings 74R are located in the center of the bending section 82. The supporting members 74, three arms of which are fixed to the inner surface of the bending section 82, are disposed at a predetermined interval. The disposition interval of the supporting members 74 is, for example, ⅓ to 1/10 of the length of the bending section 82.

The optical fiber 50 is inserted through a plurality of rings 74R.

In the endoscope 2C, as in the endoscopes 2 and 2B, the optical fiber 50 is inserted through the center of the bending section 82. Therefore, since large stress is not applied to the optical fiber 50 even if the bending section 82 is deformed, the endoscope 2C can stably transmit an optical signal.

In the endoscope 2C, a tube or the like for inserting through the optical fiber 50 is unnecessary.

Note that the plurality of supporting members 74 may be provided in the flexible portion 83 as well. A disposition interval of the supporting members 74 in the flexible portion 83 may be longer than the disposition interval in the bending section 82.

The present invention is not limited to the embodiments, the modification, and the like explained above. Various changes, combinations, and applications are possible within a range not departing from the spirit of the invention.

What is claimed is:

1. An endoscope comprising:
    an insertion section in which a rigid distal end portion, a bending section for changing a direction of the rigid distal end portion, and a flexible portion are concatenated; and
    an optical fiber that transmits an optical signal, the optical fiber being inserted through an inside of the insertion section,
    wherein an image pickup device, an optical element including a light emitting section that converts an electric signal outputted by the image pickup device into the optical signal, a holding member including a through-hole into which a distal end portion of the optical fiber is inserted and disposed to locate the through-hole on the light emitting section, and a wiring board on which the optical element is mounted and to which the holding member is joined are disposed in the rigid distal end portion so as to be located at a peripheral position deviated from a center of the rigid distal end portion, and
    the optical fiber is disposed in the rigid distal end portion so as to be inclined from the holding member, which is disposed at the peripheral position, toward the center of the rigid distal end portion, and, in the bending portion, the optical fiber is inserted through a center of the bending section.

2. The endoscope according to claim 1, further comprising a tube including a hole path inserted through the center of the bending section, wherein
    the optical fiber is inserted through the hole path.

3. The endoscope according to claim 2, wherein the tube is a multi-lumen tube including a plurality of hole paths.

4. The endoscope according to claim 1, further comprising a plurality of guide members, each including a ring disposed in the center of the bending section, wherein
    the optical fiber is inserted through the ring in plurality of the plurality of guide members.

5. The endoscope according to claim 1, wherein stress is not applied to the optical fiber even when the bending section is bent and deformed.

\* \* \* \* \*